United States Patent
Lai et al.

(10) Patent No.: US 9,629,869 B2
(45) Date of Patent: Apr. 25, 2017

(54) APPLICATION OF FRUCTUS SCHISANDRAE TOTAL POLYSACCHARIDES IN PREPARATOIN OF MEDICINE OR NUTRACEUTICALS USED FOR TREATING COUGHING

(71) Applicants: THE FIRST AFFILIATED HOSPITAL OF GUANGZHOU MEDICAL UNIVERSITY, Guangzhou (CN); GUANGZHOU INSTITUTE OF RESPIRATORY DISEASE, Guangzhou (CN); STATE KEY LABORATORY OF RESPIRATORY DISEASE, Guangzhou (CN)

(72) Inventors: Kefang Lai, Guangzhou (CN); Shan Zhong, Guangzhou (CN); Zhenyong Gan, Guangzhou (CN); Xiaodong Liu, Guangzhou (CN); Yichu Nie, Guangzhou (CN); Nanshan Zhong, Guangzhou (CN)

( * ) Notice: Subject to any disclaimer, the term of this patent is extended or adjusted under 35 U.S.C. 154(b) by 0 days.

(21) Appl. No.: 15/351,512

(22) Filed: Nov. 15, 2016

(65) Prior Publication Data

US 2017/0056431 A1    Mar. 2, 2017

Related U.S. Application Data

(63) Continuation of application No. PCT/CN2015/076064, filed on Apr. 8, 2015.

(30) Foreign Application Priority Data

May 16, 2014 (CN) .......................... 2014 1 0209951

(51) Int. Cl.
| | | |
|---|---|---|
| A61K 36/00 | (2006.01) |
| A61K 31/715 | (2006.01) |
| A61K 36/79 | (2006.01) |
| A23L 29/30 | (2016.01) |
| A23P 10/00 | (2016.01) |

(52) U.S. Cl.
CPC ............ *A61K 31/715* (2013.01); *A23L 29/30* (2016.08); *A23P 10/00* (2016.08); *A61K 36/79* (2013.01); *A23V 2002/00* (2013.01); *A61K 2236/15* (2013.01); *A61K 2236/33* (2013.01)

(58) Field of Classification Search
None
See application file for complete search history.

*Primary Examiner* — Qiuwen Mi
(74) *Attorney, Agent, or Firm* — Wayne & King LLC

(57) ABSTRACT

The present invention relates to a new application of Fructus schisandrae total polysaccharides in preparation of medicine or nutraceuticals for treating coughing, and more specifically to a new application of Fructus schisandrae total polysaccharides in preparation of medicine or nutraceuticals for preventing and relieving coughing and eliminating airway inflammation. Experiments demonstrate that the Fructus schisandrae total polysaccharides can remarkably reduce the coughing times of a guinea pig with increased cough sensitivity induced by cigarette smoke and an acute cough guinea pig induced by citric acid smoke, prolong the latent period of cough, and significantly reduce the airway inflammation of the guinea pig with increased cough susceptibility induced by cigarette smoke, so that the Fructus schisandrae total polysaccharides can be used for preparing drugs for preventing cough, relieving cough and eliminating airway inflammation.

6 Claims, 2 Drawing Sheets

APPLICATION OF FRUCTUS SCHISANDRAE TOTAL POLYSACCHARIDES IN PREPARATOIN OF MEDICINE OR NUTRACEUTICALS USED FOR TREATING COUGHING

CROSS-REFERENCE TO RELATED APPLICATIONS

This application is a continuation of International Patent Application No. PCT/CN2015/076064 with a filing date of Apr. 8, 2015, designating the United States, now pending, and further claims priority to Chinese Patent Application No. 201410209951.X with a filing date of May 16, 2014. The content of the aforementioned applications, including any intervening amendments thereto, are incorporated herein by reference.

TECHNICAL FIELD

The present invention belongs to the field of biological medicine, and relates to an application of Fructus schisandrae total polysaccharides in the preparation of medicine or nutraceuticals for treating coughing, and particularly relates to a new application of Fructus schisandrae total polysaccharides in the preparation of medicine or nutraceuticals for preventing cough, relieving cough and eliminating airway inflammation.

BACKGROUND OF THE PRESENT INVENTION

Cough is a most common symptom in internal medicine department and is found in a variety of respiratory and non-respiratory diseases. Cough itself is a defense mechanism for removing excess airway secretions and preventing foreign matters from being inhaled into the airway by mistake. However, the long-term cough may seriously influence the living quality of a patient and lead to high psychological burden to the patient and also obviously increase the personal and public medical and health expenditure.

According to the course of disease, the cough is classified into acute cough (less than 3 weeks), sub-acute cough (3-8 weeks) and chronic cough (more than or equal to 8 weeks). At present, the cough is generally treated by adopting central antitussive drug, peripheral antitussive drug, and expectorant and can generally achieve a good curative effect. However, there are still some acute and chronic coughs which cannot be relieved by adopting central antitussive drug such as codeine, resulting in conversion of acute cough into chronic cough; and moreover, the course of disease of the chronic cough patient can even reach several decades.

Many foreign epidemiological studies show that the incidence rate of chronic cough in the general population is about 9% to 33%. In 2003, a British epidemiological survey showed that the incidence rate of the chronic cough of the middle-aged people aged at 50 to 59 years reaches 12%; and the chronic cough patients accounted for about 20% of the respiratory disease outpatients. In recent years, along with the worsening of the air pollution (such as PM2.5, PM10, etc.), the incidence rate of the chronic cough is possible to increase continuously. The current study finds that main causes of the chronic cough include: cough variant asthma, eosinophilic bronchitis, gastroesophageal reflux cough and upper airway cough syndrome. The cough of a majority of patients may be obviously alleviated through the corresponding treatment according to the cough guideline for the cough caused by the above causes. However, there are still some patients with chronic cough having no obvious abnormalities after a series of comprehensive examination, but the cough symptoms persist, which is formerly known as chronic idiopathic cough (CIC); and the cough symptoms are not well alleviated and are not treated according to the causes of disease, which is the difficulty and key point in the chronic cough field at present. The study discovers that the chronic idiopathic cough is mostly found in the middle-aged people and is mostly caused by the cold, and the cough lasts for a long time; and moreover, the chronic idiopathic cough is abnormally sensitive to lampblack, pungent smells, cold air, cigarette smoke and the like, and the cough may be induced by laugh or talk sometimes, and it shows as obviously increased cough sensitivity. With regard to this situation, the chronic cough with increased cough sensitivity is named as cough hypersensitivity syndrome (CHS). The abnormal enhancement of the cough sensitivity is a common key characteristic of the CHS patients.

At present, there is no appropriate treatment means for the CHS patients to select. Most of the CHS patients are generally treated by virtue of antitussive drugs. However, the antitussive drugs such as codeine and dextromethorphan have different degrees of side effects such as constipation, sedation, respiratory depression, etc., thereby limiting its use; and moreover, some CHS patients even use the central antitussive drugs, but the cough still cannot be relieved and seriously influences the living quality of the patients in daily life.

The Fructus schisandrae is sour and sweet in taste and warm in nature. It manifests its therapeutic actions in the lung, heart and kidney meridians. Lung is a delicate organ and is averse to dryness, while the Fructus schisandrae is warm and moist and can moisten the lung to arrest cough; the chronic cough may cause the non-respiration of the kidney, while the Fructus schisandrae is sour and astringent and can help the kidney to improve the inspiration; and the effect of the Fructus schisandrae for treating the chronic cough caused by the deficiency of lung Yin and kidney Qi is great. It is recorded in "Natural Herb Collections" that: the consumptive cough should be treated by using the *Schisandra chinensis* (Turcz.) Baill., while the cold in the lung should be treated by using the *Schisandra sphenanthera* Rehd. et it is recorded in "YAOPINHUAYI" that: the Fructus schisandrae can astringe the Qi of lung and is mainly used to treat the consumptive chronic cough; and it is recorded in "Herb Sources" (BENCAOQIUYUAN) that: the Fructus schisandrae is an effective herb for treating the cough and can be used to treat cold cough, summer-heat-injured cough, dryness-causing cough, consumptive cough, renal water-deficiency cough, kidney heat deficiency cough, chronic cough and dyspnea. Zhang zhangjing clearly pointed out that all cough can be treated with the Fructus schisandrae. In "pharmacopoeia of the people's republic of china", the Fructus schisandrae can be used to treat the chronic cough and dyspnea in deficiency condition and palpitation and insomnia, in the traditional Chinese medicine, the Fructus schisandrae is widely used to treat the dry cough without phlegm at the later period of the cough or the chronic lung-deficiency cough disease.

Main chemical components of the Fructus schisandrae are volatile oils, lignans, triterpenes, organic acids and polysaccharides, wherein dibenzocyclooctene lignans and nortriterpenoid lactones are representative components of the schisandra plant. The pharmacological activity of the Fructus schisandrae is wide; there are a lot of reports about the Fructus schisandrae; and particularly, there are a lot of studies on the use of the Fructus schisandrae in protecting the liver and calming the heart and soothing the nerves.

The polysaccharide component is an important component in Fructus schisandrae herb, and its content is about 10%. It is reported that the Fructus schisandrae total polysaccharides have functions for protecting the liver, improving the immunity, resisting the senility, resisting the fatigue, preventing tumors, lowering the lipid, losing weight, resisting the oxidation, etc. However, as a component with the largest content in Fructus schisandrae herb, the Fructus schisandrae total polysaccharides are not reported about the function for relieving the cough in the literature.

SUMMARY OF PRESENT INVENTION

An objective of the present invention is to provide a new application of Fructus schisandrae total polysaccharides, and more specifically, to provide a new application of Fructus schisandrae total polysaccharides in preparation of medicine or nutraceuticals used for treating coughing.

Further, the present invention provides a new application of Fructus schisandrae total polysaccharides in preparation of medicine or nutraceuticals for treating the acute, sub-acute or chronic coughs.

Further, the present invention also provides an application of Fructus schisandrae total polysaccharides in preparation of medicine or nutraceuticals for preventing cough, relieving cough or eliminating airway inflammation.

The Fructus schisandrae total polysaccharides are extracted from the Fructus schisandrae; and by adopting a phenol-sulfuric acid detection method, the content of polysaccharides in Fructus schisandrae is 50% to 100% by mass based on D-glucose.

The Fructus schisandrae may be *Schisandra chinensis* (Turcz.) Baill. (i.e. northern Fructus schisandrae) and/or *Schisandra sphenanthera* Rehd. et. Wils (i.e. southern Fructus schisandrae).

The Fructus schisandrae total polysaccharides may be prepared into pharmaceutically acceptable dosage forms; and the example of the dosage forms is but not limited to tablets, hard capsules, soft capsules, powder, tinctures, oral solutions, syrups, granules, pills or injections. Those skilled in the art can adopt a conventional preparation process in the art to prepare the Fructus schisandrae total polysaccharides into a desired dosage form. For example, the Fructus schisandrae total polysaccharides can be made into granules by adopting the existing process: mixing the Fructus schisandrae total polysaccharides with auxiliary starch, sucrose and a disintegrating agent, adding a water-dissolved binder cellulose derivative solution and mixing, the medicine is made into soft granules by adopting an extrusion granulation method, drying the granules, screening, pulverizing the screen residue appropriately and screening again until uniform granules are prepared, and the prepared granules are subpackaged with log granules for each bag.

The Fructus schisandrae total polysaccharides are extracted from the Fructus schisandrae by adopting the existing conventional method in the art and can be prepared through the steps such as petroleum ether degreasing, water boiling, ethanol precipitation, deproteinization, decoloration, etc.

In accordance with the current situation and difficulties of the clinic treatment on the cough, a guinea pig with increased cough sensitivity induced by cigarette smoke and an acute cough guinea pig induced by citric acid smoke are used for experiments. The experimental results show that the Fructus schisandrae total polysaccharides can remarkably prolong the coughing latent period and reduce the coughing times of the guinea pig with increased cough sensitivity induced by cigarette smoke and the acute cough guinea pig induced by citric acid smoke, and remarkably reduce the total number of inflammatory cells and the ratio of neutrophil in the bronchoalveolar lavage solution of the guinea pig with increased cough sensitivity. It is noted that the inflammatory cell invasion around the guinea pig bronchiole after the intervention of the Fructus schisandrae total polysaccharides can be obviously reduced from the observation of a pathological section, the endobronchial inflammatory exudate is reduced, the broadening degree of the alveolar septum is reduced, and it shows that the Fructus schisandrae total polysaccharides has a remarkable suppression effect on the airway inflammation of the guinea pigs. Moreover, the effect of the Fructus schisandrae total polysaccharides are obviously better than that of the water extract from Fructus schisandrae, and the Fructus schisandrae total polysaccharides have a given dose-effect relationship and have the application prospect in the aspects of preventing the cough, relieving the cough and eliminating the airway inflammation. For the clinic cough hypersensitivity patients, the Fructus schisandrae total polysaccharides have an application prospect of being prepared into effective medicine for treating the patients.

DETAILED DESCRIPTION OF PREFERRED EMBODIMENTS

Figure 1:
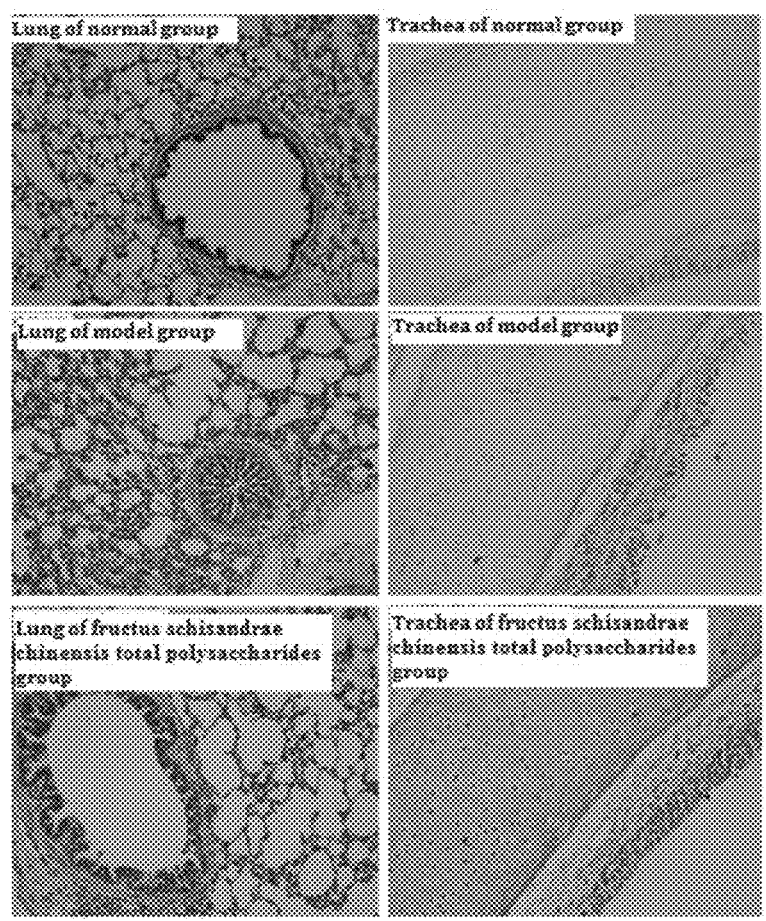
FIG. 1 is a representative graph (HE*200) of a guinea pig lung tissue and airway pathological section in embodiment I.

The present invention is further described below in details in conjunction with embodiments and drawings, but the present invention is not limited to the following embodiments.

Experimental animals used in the specific embodiments are ordinary male pure white Hartly guinea pigs each with a weight of 300±50 g which are supplied by the Laboratory Animal Center of Guangdong Province (SCXK (Guang) 2008-0002). The guinea pigs are raised in a relatively clean and quiet environment with constant temperature (23±3° C.) and constant humidity (55±15%); the diurnal cycle is 12:12 h/day; and the guinea pigs are raised in different cages, and every five guinea pigs are raised in one cage and can obtain food and water freely.

Drugs, reagents and instruments used in the specific embodiments:

(1) Fructus schisandrae total polysaccharides, the preparation steps are as follows:

Pulverizing the Fructus schisandrae, degreasing the pulverized Fructus schisandrae with petroleum ether and then decocted in water of 8-times quantity three times, concentrating the decocted liquid, precipiptating by using 80% ethanol, filtering, performing deproteinization through an enzyme precipitation method, decoloring by using active carbon, repeatedly washing by using 80% ethanol, and then drying to obtain the Fructus schisandrae total polysaccharides; and the content of the polysaccharides is 89% through test on the basis of D-glucose;

(2) water extract from Fructus schisandrae, the preparation steps are as follows:

pulverizing Fructus schisandrae→decocting for 2 h with water of eight-times quantity for three times→concentrating decocted liquid, drying→water extract from Fructus schisandrae;

(3) 0.9% sodium chloride injection: Dongguan Puji pharmaceutical co., Ltd. Pentobarbital sodium: American Merck Company. Codeine' China National Pharmaceutical Industry Co., Ltd. "Red Rose" filter-tipped cigarettes: China Tobacco Guangzhou Industrial Co., Ltd. Other conventional reagents: Guangzhou Chemical Reagent Factory.

(4) Experimental instruments: PM single-cavity nonrestrictive small animal plethysmography (1.0 L): American Buxco Company; an integrated system of digital photography: Japan Nikon Company; a 0.6 m*0.6 m*1 m cigarette smoke poisoning box: made by the laboratory; A1003 electronic scales: German Satorius Company; a MDF-U53V −80° C. low-temperature refrigerator: Japan Sanyo Company; a 3-18 k SIGMA high-speed freezing centrifugal machine: America Beckman Company; 22 G venous indwelling needles: Suzhou Medical Instrument. Co., Ltd; an Anke TGL-168-type ordinary high-speed centrifugal machine: Shanghai Anting Scientific Instrument Factory; a 400-type table-type low-temperature centrifugal machine: German Heraeus Company; XW80A-type vortex oscillator: Shanghai Precision Instrument Co., Ltd; a DK8A constant-temperature water-bath kettle: Shanghai Jinghong Test Instrument Co., Ltd.

In the detailed description, all data are expressed by using "mean value±standard deviation"; one-way analysis of variance is carried out for the comparison of different groups by using spss13.0; the homogeneity of variance is tested by using a least significant difference (LSD) method; rank sum test is adopted for non-homogeneity of variance or abnormal data; and $P<0.05$ indicates that the difference has statistical significance.

Embodiment I: Pharmacologic Action of Fructus Schisandrae Total Polysaccharides to Guinea Pigs with Increased Cough Sensitivity Induced by Cigarette Smoke 1.1 Smoking method: prior to the experiment, after being adaptively raised quietly for one week, the guinea pigs are placed in a self-made cigarette poisoning box; ten cigarettes are fired every time and placed in a smoking trough (flume-cured tobacco type, content of tar is 12 mg, content of nicotine in smoke is 1.1 mg, and content of carbon oxide in the smoke is 15 mg); and the cigarette smoke is led into the poisoning box by three-way valve, and the timing is started after the cigarette is burnt out. The guinea pigs are smoked for 20 minutes every time and twice a day; and the smoking interval time between two adjacent smoking is greater than 6 h; and the guinea pigs are consecutively smoked for 14 days.

1.2 Experiment:

The guinea pigs are randomly divided into a normal group, a model group, a solvent reference group (0.5% PEG400), a codeine group, a water extract high dose group (dose: 500 mg/kg guinea pig/day: drug concentration: 50 m/mL), a total polysaccharides high dose group (dose: 500 mg/kg guinea pig/day; drug concentration: 50 mg/mL), a total polysaccharides middle dose group (dose: 250 mg/kg guinea pig/day; drug concentration: 25 mg/mL) and a total polysaccharides low dose group (dose: 125 mg/kg guinea pig/day, drug concentration: 12.5 mg/mL).

Except for the normal group, animals in other groups are respectively stimulated by adopting the smoking method described in the above 1.1. Except for the normal group and the codeine group, the guinea pigs in the other groups are orally given with the corresponding drugs or solvent two hours before the second smoking for 14 consecutive days from the first day of smoking. The guinea pigs of the codeine group is orally administrated (30 mg/kg guinea pig; the codeine concentration: 3 mg/mL) one hour before the citric acid cough sensitivity check. The guinea pigs of the normal group are normally raised without any treatment. The guinea pigs are placed in a plethysmography box at the 15th day; two minutes later, 0.4 mol/L citric acid aqueous solution is atomized to perform the cough stimulation, and the atomizing is ended in 10 minutes; the guinea pigs are continuously observed for 10 minutes; and the coughing times and coughing latent period of the guinea pigs in 20 minutes after the atomizing is started are recorded.

Intraperitoneal injection with 3% pentobarbital sodium solution (1 mL/kg) is performed to anesthetize the animal in 24 hours after the cough stimulation test, and 10 mL of blood is taken from the heart of the animal. The bronchoalveolar lavage fluid (BALF) is obtained by taking 6 mL of 0.1 mol/L pre-cooled PBS buffer solution, performing the bronchoalveolar lavage for three times, and uniformly lavaging the left lung repeatedly for three times. The resultant BALF is shaken and suspended; 0.5 mL of the BALF is drawn to be sufficiently splitted by using red blood cell lysate and then centrifuged for 10 minutes at 3000 rpm; 10 μL of supernatant is dropped into a blood cell counting plate; a total number of BALF inflammatory cells is calculated under the optical microscope (total number of cells/mL=(total number of four lattices of cells/$4*10^4$/mL); the remaining BALF is centrifuged for 10 minutes at 3000 rpm and precipitated by using 1 mL of PBS suspension; 100 μL is used for making a cell smearer, the cell smearer is naturally dried, immersed in 10% neutral formaldehyde over a night and fixed; then the cell smearer is taken out and successively washed for 10 minutes by using flowing water, stained for 15 seconds by using hematoxylin, washed for one minute by using flowing water, decolored for 2 seconds by using 1% hydrochloric acid alcohol, washed for 10 minutes by using flowing water, stained for 5 seconds by using eosin, washed for 10 minutes by using flowing water and dried to obtain a cell smearer sealed by neutral gum; 20 neutral gum sealed smearers are consecutively and randomly extracted to be continuously counted at 400 times of magnifications under the optical microscope; 400 cells are consecutively counted on each smearer to calculate a ratio of neutrophils, eosinophils, macrophages and lymphocytes.

After the BALF is extracted from the guinea pigs, 50 mL of PBS is injected into the heart of the guinea pig to perform the lavage; 2.5 mL of 4% paraformaldehyde is injected from trachea; then a section of right lower lung tissue and a section of trachea are cut and fixed for more than 24 h by using 10% neutral formaldehyde. The fixed lung tissue is taken out and successively dehydrated by gradient ethanol, treated by biological clarifier, waxed, embedded, sectioned, dewaxed, hydrated by gradient alcohol, temporarily rinsed by double distilled water, finally stained by hematoxylin eosin (HE) and sealed by neutral gum to carry out the pathology observation.

Experimental result: compared with the normal group, the guinea pigs in each experimental group are not obviously different in airway resistance, which indicates that the experiment modeling method does not lead to the increase of the airway resistance of the guinea pigs and is different from that of a chronic obstructive pulmonary disease animal model.

The citric acid-stimulated coughing times of the guinea pigs in each experimental group is shown in table 1. The results show that, compared with the model group, the total polysaccharides (high and middle dose groups) show a significant reduction in the activity of coughing times, while the total polysaccharides at a low dose have no statistical significance on suppressing the coughing times but have a tendency of reducing the coughing times, showing a certain dose dependency: and compared with the model group, the coughing times of the guinea pigs in the water extract high-dose group have no significant difference.

TABLE 1

Impact on coughing times of the guinea pigs with increased cough sensitivity induced by cigarette smoke in each experimental group ($\bar{x} \pm s$)(n = 7-10)

| Group | Dose | Coughing times |
|---|---|---|
| Normal group | — | 32.43 ± 14.39**## |
| Model group | — | 64.29 ± 12.54 |
| Solvent reference group | 10 mL/kg | 59.86 ± 12.46 |
| Codeine group | 30 mg/kg | 37.29 ± 11.64**## |
| Water extract high dose group | 500 mg/kg | 58.43 ± 16.46 |
| Total polysaccharides high dose group | 500 mg/kg | 26.00 ± 17.31**## |
| Total polysaccharides middle dose group | 250 mg/kg | 41.71 ± 15.10*# |
| Total polysaccharides low dose group | 125 mg/kg | 49.71 ± 8.92* |

Note:
compared with the model group, *P < 0.05, and **P < 0.01; and compared with the water extract high dose group, #P < 0.05 and ##P < 0.01.

The coughing latent period of each experimental group is shown in table 2. The result shows that, compared with the model group, the total polysaccharides of a high dose, a middle dose and a low dose can remarkably prolong the coughing latent period, but the action of the water extract of a high dose on the coughing latent period is not obvious

TABLE 2

Impact on coughing latent period of the the guinea pigs with increased cough sensitivity induced by cigarette smoke in each experimental group ($\bar{x} \pm s$)(n = 7-10)

| Group | Dose | Coughing latent period (s) |
|---|---|---|
| Normal group | — | 182.28 ± 39.86**# |
| Model group | — | 80.28 ± 25.32 |
| Solvent reference group | 10 mL/kg | 85.28 ± 21.28 |
| Codeine group | 30 mg/kg | 186.14 ± 45.27**# |
| Water extract high dose group | 500 mg/kg | 106.71 ± 37.82 |
| Total polysaccharides high dose group | 500 mg/kg | 220.71 ± 52.16**## |
| Total polysaccharides middle dose group | 250 mg/kg | 189.14 ± 43.07**# |
| Total polysaccharides low dose group | 125 mg/kg | 122.57 ± 30.62* |

Note:
compared with the model group, *P < 0.05, and **P < 0.01; and compared with the water extract high dose group, #P < 0.05.

Total number of inflammatory cells in BALE and the classified comparison experimental results are shown in table 3. The results show that compared with the model group, the total polysaccharides of a high dose, a middle dose and a low dose can remarkably reduce the total number of the inflammatory cells in BALE; and the total polysaccharides of the high and middle doses can remarkably reduce the ratio of the neutrophil in the BALF. The total number of BALF cells and the classified counts of cells of the guinea pigs in the water extract high dose group are not greatly different from that of the model group.

TABLE 3

Impact on the total number and classification of BALF inflammatory cells of the the guinea pigs with increased cough sensitivity induced by cigarette smoke in each experimental group ($\bar{x} \pm s$)(n = 7-10)

| Group | total number of cells * $10^6$/mL | Mac % | Neu % | Lym % | Eos % |
|---|---|---|---|---|---|
| Normal group | 0.98 ± 0.22**## | 75.43 ± 3.36**## | 12.14 ± 2.64**## | 6.93 ± 2.73 | 5.50 ± 3.93 |
| Model group | 1.97 ± 0.36 | 44.50 ± 4.76 | 47.29 ± 5.69 | 2.79 ± 1.75 | 4.71 ± 2.33 |
| Solvent reference group | 1.92 ± 0.43 | 42.79 ± 5.45 | 46.00 ± 5.09 | 5.00 ± 1.83 | 5.43 ± 2.47 |
| Codeine group | 2.13 ± 0.38 | 43.86 ± 4.26 | 48.10 ± 3.28 | 3.64 ± 0.84 | 4.25 ± 1.36 |
| Water extract high dose group | 1.76 ± 0.36 | 46.79 ± 6.96 | 43.86 ± 4.55 | 4.57 ± 3.65 | 5.64 ± 4.39 |
| Total polysaccharides high dose group | 1.26 ± 0.28**## | 56.96 ± 6.58**## | 33.14 ± 6.98**## | 3.46 ± 1.56 | 2.57 ± 2.50 |
| Total polysaccharides middle dose group | 1.38 ± 0.32**# | 51.86 ± 5.64** | 37.64 ± 5.75**# | 4.25 ± 3.23 | 2.61 ± 2.30 |
| Total polysaccharides low dose group | 1.54 ± 0.40* | 47.86 ± 6.65 | 42.00 ± 5.17 | 2.89 ± 1.85 | 3.75 ± 2.75 |

Note:
compared with the model group, *P < 0.05, and **P < 0.01; and compared with the water extract high dose group, #P < 0.05 and ##P < 0.01.

The observation result of the pathological section shows that, compared with the model group, the pathology of the lung tissues and trachea of the guinea pigs given with different doses of the total polysaccharides are obviously improved: the inflammatory cell invasion around the bronchiole of the guinea pigs is obviously reduced, the endobronchial inflammatory exudate is alleviated, the alveolar septum broadening degree is reduced, which indicates that the Fructus schisandrae total polysaccharides have an obvious action on alleviating the lung and airway inflammation. But the pathology of the lung tissues and trachea of the guinea pigs given with high dose of water extract is not obviously improved. The guinea pig tissue and trachea pathological section representative graph is shown in FIG. 1.

The experimental result of embodiment I shows that the Fructus schisandrae total polysaccharides have an obvious action on reducing the coughing times, prolonging the latent period of cough and alleviating the lung and airway inflammation to the guinea pigs with increased cough sensitivity induced by cigarette smoke.

Embodiment II

After the guinea pigs are quietly raised for one week, the cough sensitivity screening is carried out: the guinea pigs is stimulated for one minute by atomizing 0.8 mol/L citric acid and continuously observed for five minutes; the coughing times of the guinea pigs in 6 minutes after the atomizing is started is recorded; and the guinea pigs with the coughing times greater than 10 times and less than 50 times are the qualified guinea pigs.

The qualified guinea pigs are selected to be randomly divided into a normal group, a solvent reference group (0.5% PEG400), a codeine group, a water extract high dose group (dose: 500 mg/kg guinea pig day: drug concentration: 50 mg/mL), a total polysaccharide high dose group (dose: 500 mg/kg guinea pig/day; drug concentration: 50 mg/mL), a total polysaccharide middle dose group (dose: 250 mg/kg guinea pig/day: drug concentration: 25 mg/mL) and a polysaccharide low dose group (dose: 125 mg/kg guinea pig/day: drug concentration: 12.5 mg/mL).

Except for the normal group and the codeine group, the guinea pigs in the rest groups are orally given with drugs or solvent consecutively for five days and once a day; and the citric acid cough stimulation is carried out in one hour after the guinea pigs are given with the drug or solvent at the fifth day: the guinea pigs are stimulated for one minute by atomizing 0.8 mol/L citric acid and are continuously observed for 5 minutes after the atomizing is stopped, and the coughing times of the guinea pigs in 6 minutes after the atomizing is started is recorded. The guinea pigs of the codeine group are orally given with the drug in one hour before the citric acid cough stimulation at the fifth day. The guinea pigs of the normal group are raised normally and are directly stimulated by the citric acid at the fifth day.

The coughing times of the guinea pigs in each experimental group are shown in table 4. The result shows that, compared with the normal group, the coughing times of the guinea pigs intervened with the high dose, middle dose and low dose of total polysaccharides is remarkably reduced, while the coughing times of the guinea pigs intervened with the high dose of water extract has no significant difference.

TABLE 4

Impact on the coughing times of the acute cough guinea pigs induced by citric acid smoke ($\bar{x} \pm s$) (n = 8)

| Group | Dose | Coughing times |
|---|---|---|
| Normal group | — | 24.00 ± 4.90 |
| Solvent reference group | 10 mL/kg | 21.67 ± 4.46 |
| Codeine group | 30 mg/kg | 3.83 ± 1.94**## |
| Water extract high dose group | 500 mg/kg | 19.17 ± 4.36 |
| Total polysaccharides high dose group | 500 mg/kg | 3.50 ± 1.87**## |
| Total polysaccharides middle dose group | 250 mg/kg | 7.5 ± 3.27**## |

TABLE 4-continued

Impact on the coughing times of the acute cough guinea pigs induced by citric acid smoke ($\bar{x} \pm s$) (n = 8)

| Group | Dose | Coughing times |
|---|---|---|
| Total polysaccharides low dose group | 125 mg/kg | 12.17 ± 3.19**## |

Note:
compared with the normal group, **$P < 0.01$; and compared with the water extract high dose group, ##$P < 0.01$.

The coughing latent period of the guinea pigs in each experimental group is shown in table 5. The results show that, compared with the normal group, the coughing latent period of the guinea pigs intervened with the high dose, middle dose and low dose of total polysaccharides is remarkably prolonged, while the coughing latent period of the guinea pigs intervened with high dose of water extract has no significant difference.

TABLE 5

Impact on the coughing latent period of the acute cough guinea pigs induced by citric acid smoke ($\bar{x} \pm s$) (n = 8)

| Group | Dose | Coughing latent period (s) |
|---|---|---|
| Normal group | — | 39.67 ± 13.53 |
| Solvent reference group | 10 mL/kg | 31.17 ± 13.23 |
| Codeine group | 30 mg/kg | 115.3 ± 20.18**## |
| Water extract high dose group | 500 mg/kg | 42.69 ± 10.76 |
| Total polysaccharides high dose group | 500 mg/kg | 132.3 ± 40.51**## |
| Total polysaccharides middle dose group | 250 mg/kg | 104.5 ± 22.51**## |
| Total polysaccharides low dose group | 125 mg/kg | 68.33 ± 17.14**# |

Note:
compared with the normal group, *$P < 0.05$, and **$P < 0.01$; and compared with the water extract high dose group, #$P < 0.05$ and ##$P < 0.01$.

The results of embodiment II show that the Fructus schisandrae total polysaccharides can remarkably reduce the coughing times and can prolong the coughing latent period of the acute cough guinea pigs induced by citric acid smoke, and show an application potential in the aspect of treating the acute cough.

Embodiment III

After the guinea pigs are quietly raised for one week, the cough sensitivity is screened: the guinea pigs are stimulated for one minute by atomizing 0.8 mol/L citric acid and continuously observed for five minutes after the atomizing is stopped; the coughing times of the guinea pigs in 6 minutes after the atomization is started is recorded; and the guinea pigs with the coughing times greater than 10 times and less than 50 times are the qualified guinea pigs.

Figure 2:
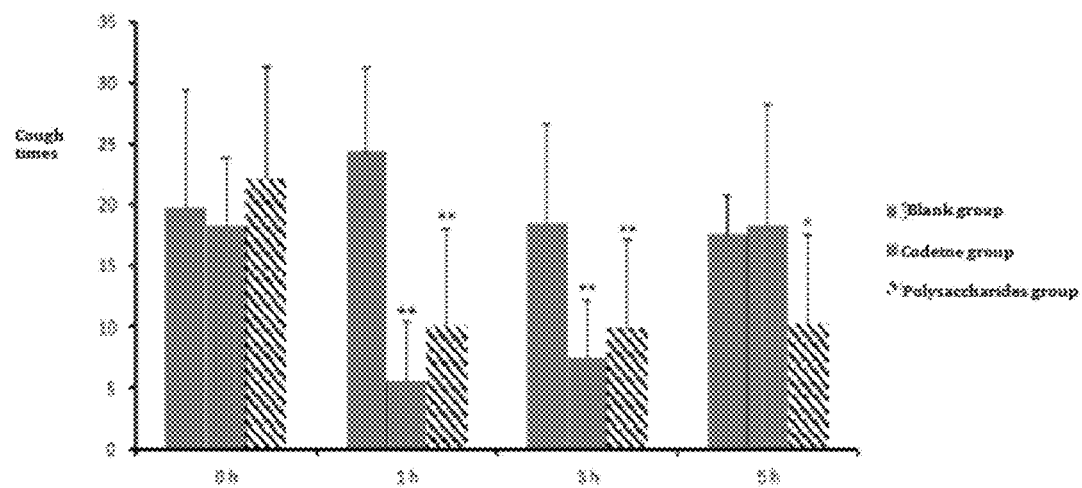
FIG. 2 is a graph showing the impact of the Fructus schisandrae total polysaccharides on the coughing times of citric acid smoke stimulation-caused guinea pigs at different time points.

The qualified guinea pigs are selected to be normally raised for three days and randomly divided into four groups with 30 guinea pigs in each group. The guinea pigs in the first group are divided into three subgroups with 10 guinea pigs in each subgroup, and all guinea pigs are directly under the citric acid cough stimulation: the guinea pigs are stimulated for one minute by atomizing 0.8 mol/L citric acid and are continuously observed for 5 minutes after the atomization is stopped, and the coughing times of the guinea pigs in 6 minutes after the atomization is started is recorded. The guinea pigs in the second group are randomly divided into three subgroups, i.e. a normal group, a codeine group (30 mg/kg, oral administration), a Fructus schisandrae total polysaccharides group (500 mg/kg, drug concentration: 50 mg/mL, orally administration), and each subgroup contains 10 guinea pigs; the normal group is directly under the citric acid cough stimulation; the codeine group and the Fructus schisandrae total polysaccharides group are under the cough stimulation in one hour after being administrated, and the stimulation condition is the same with that of the first group; and the grouping and stimulation conditions of the third group and the fourth group are the same with that of the second group, and the codeine group and the Fructus schisandrae total polysaccharides group are respectively administrated in three hours and five hours before the stimulation. The results are as shown in FIG. 2 and show that the acute coughing times of the citric acid smoke stimulation-caused guinea pigs can be remarkably reduced in one hour after the guinea pigs are given with the Fructus schisandrae total polysaccharides (500 mg/kg) for one time: the drug effect is still significant in 5 hours after the Fructus schisandrae total polysaccharides are administrated; and the coughing times of the guinea pigs in 5 hours after the guinea pigs are given with the codeine have no significant difference with that of the normal group.

As can be seen from embodiment I to embodiment III, the Fructus schisandrae total polysaccharides can remarkably prolong the latent period of the cough and reduce the coughing times of the guinea pigs with increased cough sensitivity induced by cigarette smoke and the acute cough guinea pig induced by citric acid smoke, prolong the latent period of cough, and can remarkably reduce the total number of inflammatory cells and the ratio of neutrophil in the bronchoalveolar lavage solution of the guinea pigs with increased cough sensitivity induced by cigarette smoke. It is noted that the inflammatory cell invasion around the guinea pig bronchiole after the intervention of the Fructus schisandrae total polysaccharides can be obviously reduced from the observation of a pathological section, the endobronchial inflammatory exudate is reduced, the broadening degree of the alveolar septum is reduced, and it shows that the Fructus schisandrae total polysaccharides has a remarkable suppression effect on the airway inflammation of the guinea pigs. Moreover, the effect of the Fructus schisandrae total polysaccharides is obviously better than that of water extract from Fructus schisandrae, and the Fructus schisandrae total polysaccharides have a given dose-effect relationship and have the application prospect in the aspect of preventing cough, relieving cough and eliminating airway inflammation.

Embodiment IV (an Example of Preparing Syrup Containing the Fructus Schisandrae Total Polysaccharides)

2 kg of Fructus schisandrae total polysaccharides are dissolved in an appropriate amount of water to prepare a Fructus schisandrae total polysaccharides solution for standby use; 2 kg of sucrose is boiled in water and uniformly mixed with the prepared Fructus schisandrae total polysaccharides solution and 4 g of sodium benzoate and stands, the supernatant is uniformly mixed with water to reach 2000 mL to obtain Fructus schisandrae total polysaccharides syrup. The syrup is sub-packaged with 100 mL in each bottle.

Method for taking the syrup: the syrup is taken one to three times a day with 10 mL for each time, and the amount of the syrup for the patient in a serious condition can be increased appropriately.

In the present embodiment, the Fructus schisandrae total polysaccharides are prepared by adopting the extraction process described hereinabove and prepared in the following specific steps: the Fructus schisandrae is pulverized, the pulverized Fructus schisandrae is degreased with petroleum ether and then decocted in 8 times water for three times, the decocted liquid is concentrated, the concentrated liquid is precipitated by using 80% ethanol, filtered, deproteinized through an enzyme precipitation method, decolored by using active carbon, repeatedly washed by using 80% ethanol, and then dried to obtain the Fructus schisandrae total polysaccharides; and the content of the polysaccharides is 89% through test on the basis of D-glucose.

Application Example

The Fructus schisandrae total polysaccharides syrup prepared in the embodiment IV has already been clinically tested, wherein there are 12 cases of chronic cough patients and 11 cases of acute cough patients; the patients drink the syrup prepared in the embodiment IV one to three times a day with 10 mL at each time consecutively for one to two weeks, the total effective rate is 100%, and the specific feedback results are shown in the table below.

| Case | Excellent effect | Effective | Noneffective |
| --- | --- | --- | --- |
| acute cough | 8 | 3 | 0 |
| chronic cough | 9 | 3 | 0 |

Three typical cases are described in detail below:

Case 1: Mr. Wen, Male, 50 years old, coughing for about three months, diagnosed with cough hypersensibility syndrome, and continuously taking the Fructus schisandrae total polysaccharides syrup for one week; the cough sensitivity is remarkably alleviated, and the coughing times are significantly reduced.

Case 2: Mr. Xi, 25 years old, coughing for about one month, diagnosed with post-cold cough, and taking two bottles of the Fructus schisandrae total polysaccharides syrup; and the syrup takes effect at the first day, and the cough is basically alleviated.

Case 3: Mrs. Kong, 46 years old, coughing for about one month, having sputum obstruction, difficult to cough up the sputum, diagnosed with post-infective cough, and taking two bottles of the Fructus schisandrae total polysaccharides syrup; and the syrup takes effect at the second day, the patient gets better by 70%, and after taking one more bottle of syrup, the cough of the patient is basically completely alleviated.

Case 4: Mr. Yu, 36 years old, coughing for about one year, having dry cough, diagnosed with eosinophils bronchitis, having gastroesophageal reflux cough and taking two bottles of Fructus schisandrae total polysaccharides syrup; the drug takes effect at the third day; the patient gets better by 40%; and after the patient takes two bottles of Fructus schisandrae total polysaccharides syrup, the cough symptom is basically eliminated.

As is known from the above embodiments, the cough can be effectively relieved by orally taking the Fructus schisandrae total polysaccharides syrup, and the airway inflammation can be alleviated. Moreover, the Fructus schisandrae total polysaccharides are extracted from the traditional Chinese medicine Fructus schisandrae; and the Fructus schisandrae is the traditional Chinese medicine available for the health food published by the ministry of health and has no toxicity and side effect to the human body. The Fructus schisandrae total polysaccharides are made into syrup and also can be made into other pharmaceutically acceptable dosage forms by those skilled in, the art according to the need such as tablets, hard capsules, soft capsules, powder, tinctures, pills, granules, injections or other orally liquid forms.

The above only describes preferred embodiments of the present invention, and is not intended to limit the present invention in any form. Therefore, any simple alteration, equivalent changes and modifications made to the above embodiments based on the technical essence of the present invention without departing from the technical solution of the present invention shall still belong to the scope of the technical solution of the present invention.

We claim:

1. An application of Fructus schisandrae total polysaccharides in preparation of medicine or nutraceuticals used for treating coughing, characterized in that the medicine or nutraceuticals are used for treating acute cough, sub-acute cough or chronic cough; and the Fructus schisandrae total polysaccharides are prepared through the following steps: pulverizing Fructus schisandrae, degreasing the pulverized Fructus schisandrae with petroleum ether, decocting the degreased Fructus schisandrae for three times by using 8 times water, concentrating obtained decocted liquid, precipitating the concentrated solution by using 80% ethanol, filtering, performing deproteinization through a precipitation enzymatic method, decoloring by using active carbon, repeatedly washing by using 80% ethanol, and then drying to obtain the Fructus schisandrae total polysaccharides, and the content of polysaccharides in the Fructus schisandrae total polysaccharides is 89% through test on the basis of D-glucose.

2. The application according to claim 1, characterized in that the medicine or nutraceuticals are used for preventing cough, relieving cough or eliminating airway inflammation.

3. The application according to claim 1, characterized in that the Fructus schisandrae total polysaccharides are extracted from Fructus schisandrae, and the Fructus schisandrae is at least one of *Schisandra chinensis* (Turcz.) Baill. and *Schisandra sphenanthera* Rehd. et Wils.

4. The application according to claim 1, characterized in that the Fructus schisandrae total polysaccharides are made into pharmaceutically acceptable dosage forms.

5. The application according to claim 4, characterized in that dosage forms are tablets, hard capsules, soft capsules, powder, tinctures, oral solutions, syrups, granules, pills or injections.

6. The application according to claim 2, characterized in that the Fructus schisandrae total polysaccharides are extracted from Fructus schisandrae, and the Fructus schisandrae is at least one of *Schisandra chinensis* (Turcz.) Baill. and *Schisandra sphenanthera* Rehd. et Wils.

* * * * *